US007148401B2

(12) United States Patent
Multani et al.

(10) Patent No.: US 7,148,401 B2
(45) Date of Patent: Dec. 12, 2006

(54) BRACHYTIC2 (BR2) PROMOTER FROM MAIZE AND METHODS OF USE

(75) Inventors: Dilbag Multani, Urbandale, IA (US); Xiaomu Niu, Johnston, IA (US); Dwight T. Tomes, Van Meter, IA (US); Haiyin Wang, Johnston, IA (US); Deping Xu, Johnston, IA (US)

(73) Assignees: Pioneer Hi-Bred International, Inc., Johnston, IA (US); The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 10/931,077

(22) Filed: Aug. 31, 2004

(65) Prior Publication Data

US 2005/0204432 A1    Sep. 15, 2005

Related U.S. Application Data

(60) Provisional application No. 60/499,580, filed on Sep. 2, 2003.

(51) Int. Cl.
*C12N 15/82*   (2006.01)
*C07H 21/04*   (2006.01)
*A01H 5/00*    (2006.01)

(52) U.S. Cl. .................. 800/287; 800/278; 800/290; 435/468; 435/419; 435/320.1; 536/24.1

(58) Field of Classification Search ............... 800/287, 800/278; 536/24.1; 435/69, 1
See application file for complete search history.

(56) References Cited

U.S. PATENT DOCUMENTS 6,307,126 B1   10/2001   Harberd et al.

FOREIGN PATENT DOCUMENTS

| WO | WO 99/09174 A1 | 2/1999 |
| WO | WO 00/09706 A2 | 2/2000 |
| WO | WO 01/34818 A2 | 5/2001 |
| WO | WO 01/34819 A2 | 5/2001 |

OTHER PUBLICATIONS

Kim Y, Buckley K, Costa MA, and An G. A 20 nucleotide upstream element is essential for the nopaline syntase (nos) promoter activity. (1994) Plant Molecular Biology, vol. 24, pp. 105-117.*
Bennetzen, J., et al., "Molecular Cloning of Maize Genes by Transposon Tagging with *Mutator*," *Plant Gene Systems and Their Biology*, 1987, pp. 183-204.
Campbell, et al., "Effects of a Single Height Gene dw-3 of Sorghum on Certain Agronomic Characters," *Crop Science*, 1975, pp. 595-597, vol. 15(4).
Davies, et al., "Cloning and Characterization of a Novel P-glycoprotein Homologue from Barley," *Gene*, 1997, pp. 195-202, vol. 199(1-2), Amsterdam.

Dudler, R. and C. Hertig, "Structure of an mdr-like Gene from *Arabidopsis thaliana*," *J. Biological Chemistry*, 1992, pp. 5882-5888, vol. 267(9), The American Society for Biochemistry and Molecular Biology, Inc.
Fu, X., et al., "Expression of Arabidopsis GAI in Transgenic Rice Represses Multiple Gibberellin Responses," *The Plant Cell*, 2001, pp. 1791-1802, American Society of Plant Biologists.
Holland, N., et al., "A Comparative Analysis of the Plant Cellulose Synthase (*CesA*) Gene Family," *Plant Physiology*, 2000, pp. 1313-1323, vol. 123, American Society of Plant Physiologists.
Huttly, A. and A.L. Phillips, "Gibberellin-regulated Plant Genes," *Physiologia Plantarum*, 1995, pp. 310-317, vol. 95, Denmark.
Ikeda, A., et al., "*slender* Rice, a Constitutive Gibberellin Response Mutant, is Caused by a Null Mutation of the *SLR1* Gene, an Ortholog of the Height-Regulating Gene *GAI/RGA/RHT/D8*," *The Plant Cell*, 2001, pp. 999-1010, vol. 13, American Society of Plant Physiologists.
Morita, A., et al., "Functional Dissection of a Sugar-repressed α-amylase gene (*RAmylA*) Promoter in Rice Embryos," *FEBS Letters*, 1998, pp. 81-85, vol. 423, Federation of European Biochemical Societies.
Peng, J., et al., "The *Arabidopsis GAI* Gene Defines a Signaling Pathway that Negatively Regulates Gibberellin Responses," *Genes & Development*, 1997, pp. 3194-3205, vol. 11, Cold Spring Harbor Laboratory Press.
Peng, J., et al., "'Green Revolution' Genes Encode Mutant Gibberellin Response Modulators," *Nature*, 1999, pp. 256-261, vol. 400, Macmillan Magazines Ltd.
Sidler, M., et al., "Involvement of an ABC Transporter in a Developmental Pathway Regulating Hypocotyl Cell Elongation in the Light," *The Plant Cell*, 1998, pp. 1623-1636, vol. 10, American Society of Plant Physiologists.
Smart, C.C., and A.J. Fleming, "Hormonal and Environmental Regulation of a Plant PDR5-like ABC Transporter," *J. Biological Chemistry*, 1996, pp. 19351-19357, vol. 271(32), The American Society for Biochemistry and Molecular Biology, Inc.
Spray, C., et al., "Cloning a Maize Dwarfing Gene by Transposon Tagging," *Plant Physiology*, 1995, p. 132, vol. 108(2), Annual Meeting of the American Society of Plant Physiologists.
Theodoulou, F.L., "Plant ABC Transporters," *Biochimica et Biophysica Acta*, 2000, pp. 79-103, vol. 1465, Elsevier Science B.V.
Wang, W., et al., "A Potato cDNA Encoding a Homologue of Mammalian Multidrug Resistant P-glycoprotein," *Plant Molecular Biology*, 1996, pp. 683-687, vol. 31, Kluwer Academic Publishers, Belgium.

(Continued)

*Primary Examiner*—Ashwin D. Mehta
*Assistant Examiner*—Cathy Kingdon Worley
(74) *Attorney, Agent, or Firm*—Alston & Bird LLP

(57) ABSTRACT

The invention relates to the regulation of gene expression, particularly to methods and compositions for regulating gene expression in plants. Expression cassettes comprising a polynucleotide molecule of interest operably linked to the Brachytic2 (Br2) promoter, or a functional fragment or variant thereof, are provided. Methods of using such expression cassettes, as well as plant cells, plant tissues, plants, and seeds transformed with these expression cassettes, are additionally provided. The methods and compositions find use in regulating the expression of a polynucleotide molecule of interest in a plant.

21 Claims, 13 Drawing Sheets

OTHER PUBLICATIONS

Winkler, R.G., and T. Helentjaris, "The Maize *Dwarf3* Gene Encodes a Cytochrome P450-Mediated Early Step in Gibberellin Biosynthesis," *The Plant Cell*, 1995, pp. 1307-1317, vol. 7, American Society of Plant Physiologists.

Genbank Report for Accession No. Y10227, Direct submission May 19, 1997.

Genbank Report for Accession No. Y10228, Direct submission May 19, 1997.

Genbank Report for Accession No. Y10099, Direct submission Oct. 24, 1997.

Genbank Report for Accession No. Y15193, Direct submission Nov. 1, 1997.

Genbank Report for Accession No. Y15194, Direct submission Nov. 1, 1997.

Genbank Report for Accession No. Y15990, Direct submission Dec. 28, 1997.

Genbank Report for Accession No. X61370, Direct submission Nov. 9, 1998.

Genbank Report for Accession No. U52079, Direct submission Feb. 1, 1999.

Genbank Report for Accession No. AJ242530, Direct submission Jul. 28, 1999.

Genbank Report for Accession No. AJ242531, Direct submission Jul. 28, 1999.

Genbank Report for Accession No. AF200525, Direct submission Aug. 31, 2000.

Genbank Report for Accession No. AF200528, Direct submission Aug. 31, 2000.

Genbank Report for Accession No. AF200532, Direct submission Aug. 31, 2000.

Genbank Report for Accession No. AB030956, Direct submission Mar. 21, 2002.

\* cited by examiner

FIGURE 1A

```
           --------Forward Primer---->
CTTTCAATTAAGTTGAGTCGGGGGTAGATTCTCAAGGCTACATAAATAGTTTTTTTCT
AGAATGGATGCATTTGTTTAAGAGAAAAATGATGCACTTGGATGCATCAAGCAAAGGGA
TGTAAGAATGTTGAAAAAACACATGACCCGTATCGGCGAGATGCTTATTTATCCATTCT
TTATCACAGGGATGCATATGCAACAAAACCAAAACAGATGGTTAGCGAGTGACAGTATA
TAGAGATCTAAAGTTGTCCGACACTTCATCGGTAAAAAAAGCAGCATAACCGAGTGAAT
GCAAGAAAAACGAATTTCTCATATACACAGCAGGTTTTCTTAAAAAACGTTATATCGGT
ATTATATTAAGAAGAGACCAAAATATGGTCCTGTCGAGAAAATTTATAAACATTAGTTC
TCATCACCAGTGAGCCGTCACCATCTAGTTTGCAACGGTCCAGTTAGAGTGCACTCAGG
ACTCGCAGCGAGAGAATTTTTTAATCAAGCCTAAAATTCACTTTCGGACAAATCGAAC
TACTCATAAATATTAACCATGAGACCTTTTCGCCGCAGCAGGTTTTCTATCGGCCGTTA
GATTTAGTGACGATGAAAATGATAGAACGCAACGTGCCGCATGCATCCATTCCCATTC
GTTTTCCACAGTACATGTAGGAGTACTGTGCAAGTAGGGTCCGTACATTCAGTCTCTCT
CACTAGTTGGATTCTTCTAATGCTACAAAGACATGAGCTGCCGGGAATGGGAACCGGAG
GAGCGAGCGAGCCTGGCGGTCTCACACACACAGTCACACTCCCAAGCCAATTATTATAA
GAGGGGAGATGAGCAACTCCAGCTCTTAANCCAATCCACTCCTCCTCCCTCTCCACCTC
ATATGCTTTGCTCTGCCACTCTGCTGAGGTGGGGGGCAGAGGAGCTCCCCCTCCCTCCT
CTCCCCTCCTCGCCATGTCTAGCAGCGACCCGGAGGAGATCAGGGCGCGCG
           <--Reverse Primer--
```

FIGURE 1B

```
                    EcoRI
GSP-F1    5'-TATGAATTCGAGTCGGGGGTAGATTCTCAAGGCTAC-3'

GSP-R1 5'    TATAACCATGGATCCGAGGAGGGGAGAGGAGGGAG-3'
                NcoI   BamHI
```

FIGURE 2

AGAGCGGTTGTTCCCAAAAAAGGTGCAAATTCTCCAATTCCCCTTCACTCGAATTTTGG
CCGTAAGCGTGAGTCATAAATCTGACGAAATAAAAATAATTGTACAGTTTGATCAGAAT
TGACGGGATAATCTTTGAGTCTAGTAGCCCATGATTGGATAATATTTGTCAAATACAAA
CGAAAAAGCTAAGGCCTTGTTTAGATGCACCTAAAAACCCAAAACTGTTACAAGATTCC
CCATCACATCGAATCTTGTGGCACATGCATGGAATATTAAATCTAGATAAAAAGATAA
GTAATTATACAGGTTACCTGTAAATCACGGTACAAATCTAAAAAGACGAAAATGGTACG
GTGTCAAAATCTAAAAAGTTTTTGCATCTAAACAAGGGCCTTGTTTAGTTCGCAAAATT
TTTTAAGATTTCCCGTCACATCGAATCTTTGGTCGTATGCATGGAGCATTAAATATAGA
TAAAAATAAAAACTAATTGCACAGTTTACCTGTAATTTGTGAGATGAATCTTTTGAGCC
TAGTTACTCCATGATTGGACAATGTTTGTCAAATAAAAACAAAAGTGGTACAGTAGTCA
AAAACCAAAGTTTTTGCCAACTAAACGAGGCCTAGGCCTAATTGCACATTTTGACTGTA
AATCGCGAGACGAATCTTTGAAAACTTTTTATACGTCTTGTTTAGTTCACCCTTAAAAA
CCAAAATTTTTTCAAGATTCTCCGTCATCGGATTCTTTTGCCACAAACATGGCCCTTAA
AATAGATGAAAACCAACCTTAATTGTACAGTTTGTTGTAATTCGGAGAGGAATCTTTTA
ATCTAGTTACTGTATGATTGAATAATGTTTGTTAAATAAAAATGAAAGTGCCTTACACC
GGTCCTCAGCGAAGGAAGAAACACGAATTTTTTGTAGAGCACAAGCACAAAAGGTTTCC
CATCGGCCATAGATTTTCGTGACGACATTGATAGAACGCAACGCGTAGAATACATCCAT
TCTCGTTCGTTTTCCACAGTATGGGGATGAGTACTGTACTGTGCAAGGAGCCCCCCCGT
ACATTCACAGTCTCTCTCACTCGTTGGACTCTTCCTCTACTCCTACAAAGACACACGAG
GCTGCCTGGGATTGGAGCCTTGCACTGGGCCGACGCCGACCGGACGGCCGAGCGAACGA
GCCTGAACCAGAGCCCCTCTCATCAGAGGTCTCAAGCCGCAAGCCAATTATAAGAGGCG
AGACAAAGCAACTCCCAATTCAATCCACCCCAGGGCCTCCCTCCCTCCCTCTCGGCATC
CTCTGCTTTGCTCTGCGCCAGCCACTCTTCCGAGGTGGGGCAGAGGAGAGGAGAGCTT
CCCCCCCTCCCTTCCCTCGGTCCCTTCCCCGGCCCCCGATCGATGTCTACCAACGAC
CCGGACGAGATCAGGGCGCGCGTCGTCGTCCTCGGCGCCCTCAT

GCG: BestFit DNA Alignment Analysis

>Br2-Promoter from: 1 to: 961

>Dw3-Promoter from: 1 to: 1404

```
         Gap Weight:      50      Average Match:    10.000
      Length Weight:       3      Average Mismatch: -9.000

Maximum penalized length: 12

Quality:    1506            Length:    1439
               Ratio:   1.590              Gaps:      29
  Percent Similarity:  76.786    Percent Identity:  76.607

Average quality based on 10 randomizations: 137.8 +/- 23.7

Match display thresholds for the alignment(s):
                      | = IDENTITY
                      : = 5
                      . = 1

1 CTTTCAATTAAGTTGAGTCGGGGGTAGATTCTCAAGGCTACATAAATAGT  50
      | ||| |      || ||   | |            |  |||| |||
  324 GGTACAAATCTAAAAAGACGAAAATGGTACGGTGTCAAAATCTAAAAAGT 373

51 TTTTTTTCTAGAATGGATGCATTTGTTTAAGAGAAAAATGATGCACTTGG 100
      |||
  374 TTT............................................... 376

101 ATGCATCAAGCAAAGGGATGTAAGAATGTTGAAAAAACACATGACCCGTA 150
      |||||| |   |||||
  377 .TGCATCTAAACAAGGG.................................. 392

151 TCGGCGAGATGCTTATTT................................ 168
             ||| |||
  393 .........CCTTGTTTAGTTCGCAAAATTTTTTAAGATTTCCCGTCAC 432

169 ATCCATTCTTTATCACAGGGATGCATATGCAACAAAACCAAAACAGATGG 218
      ||| | |||||                                  | | |
  433 ATCGAATCTTT...............................GGTCG 448

219 TTAGCGAGTGACAGTATATAGAGATCTAAAGTTGTCCGACACTTCATCGG 268
      |  ||  |    || ||  ||| ||||   |
  449 TATGCATGGAGCATTAAATATAGATAAA...................... 476

269 TAAAAAAAGCAGCATAACCGAGTGAATGCAAGAAAAACGAATTTCTCATA 318
                                  || ||||||| |||| | ||
  477 ............................AATAAAAACTAATTGCACA... 495

319 TACACAGCAGGTTT.................................... 332
                ||||
  496 ..........GTTTACCTGTAATTTGTGAGATGAATCTTTTGAGCCTAGT 535
```

```
333  ..........................TCTTAAAAAACGTTATATCGGT  354
                               ||||  ||||| || |||  ||
636  ACATTTGACTGTAAATCGCGAGACGAATCTTTGAAAACTTTTTATACGT  685

355  ATTATATTAAGAAGAGACCAAAATATGGTCCTGTCGAGAAAATTTATAAA  404
       || |
686  CTTGT............................................  690

405  CATTAGTTC.....TCATCACCAGTGAGCCGTCACCATCTAGTTTGCAAC  449
     |||||||      | |  ||||
691  ..TTAGTTCACCCTTAAAAACCA...........................  711

450  GGTCCAGTTAGAGTGCACTCAGGACTCGCAGCGAGAGAATTTTTTAA...  497
                                      |||||||||  ||
712  ................................AAATTTTTTCAAGA   725

498  TCAAGCCTAAAATTCACTTTCGGACAAATCGAACTACTCATAAATATTAA  547
     |||||    ||||
926  ACAAGCACAAAA......................................  937

548  CCATGAGACCTTTTCGCCGCAGCAGGTTTTCTATCGGCCGTTAGATTTTA  597
                              |||||  |  |||||||||  ||||||||
938  .....................GGTTTCCCATCGGCC.ATAGATTTTC  962

598  GTGACGATGAAAATGATAGAACGCAACGTGCCGCATGCATCCATTCCCAT  647
     |||||    || |  ||||||||||||||||  |  | ||  |||||||||  | |
963  GTGAC...GACATTGATAGAACGCAACGCGTAGAATACATCCATTCTCGT  1009

648  TCGTTTTCCACAGTACATGTAGGA.....GTACTGTGCAAGTAG..GGTC  690
     ||||||||||||||    | | ||       ||||||||||||| ||    |
1010 TCGTTTTCCACAGTATGGGGATGAGTACTGTACTGTGCAAGGAGCCCCCC  1059

691  CGTACATT..CAGTCTCTCTCACTAGTTGGA...TTCTTCTAATGCTACA  735
     ||||||||   |||||||||||||||  ||||||     |||  ||||  |  |||||
1060 CGTACATTCACAGTCTCTCTCACTCGTTGGACTCTTCCTCTACTCCTACA  1109

736  AAGACA...TGAGCTGCCGGGAATGGGAAC....................  762
     ||||||      ||||||  ||  ||||  |
1110 AAGACACACGAGGCTGCCTGGGATTGGAGCCTTGCACTGGGCCGACGCCG  1159

763  ......CGGAGGAGCGAGCGAGCCTG...................GCGG  786
           |||  |||||| |||||||||                    | ||
1160 ACCGGACGGCCGAGCGAACGAGCCTGAACCAGAGCCCCTCTCATCAGAGG  1209

787  TCTCACACACACAGTCACACTCCCAAGCCAATTATTATAAGAGGGGAGA.  835
     |||||          |   | ||||||||    ||||||||||   ||||
1210 TCTCA.............AGCCGCAAGCCAA...TTATAAGAGGCGAGAC  1243

836  TGAGCAACTCCAGCTCTTAANCCAATCCACTCC...........TCCTCC  874
     ||||||||||       ||:|||||||| ||            |||||
1244 AAAGCAACTCC.......CAATTCAATCCACCCCAGGGCCTCCCTCCCTCC  1287
```

```
 875 CTCTCCACCTCATATGCTTTGCTCT......GCCACTCTGCTGAGGTGGG  918
     ||||  |  || |  |||||||||||      |||||||| |  ||||| ||
1288 CTCTCGGCATCCTCTGCTTTGCTCTGCGCCAGCCACTCTTCCGAGGT.GG 1336

919 GGGCAGAGGAG..........CTCCCCCTCCCTCCTCTC  947..........ATG
     ||||||||||          |  ||||||||||| |  |||
1337 GGGCAGAGGAGAGGAGAGCTTCCCCCCCTCCCTTCCCTC 1375..........ATG
```

Conserved Sequence Motifs Between Maize Br2 And Sorghum Dw3 Promoters

FIGURE 4B

Dw3 Promoter

| Motif | Site | Position |
|---|---|---|
| 1 | gccactcttccgaggtggggg (SEQ ID NO: 3) | 1319 to 1339 |
| 2 | Tgatagaacgcaacgcgtagaatacatccattctcgttcgttttccacagt (SEQ ID NO: 4) | 973 to 1023 |
| 3(a) | cagtctctctcactcgttggactcttc (SEQ ID NO: 5) | 1070 to 1096 |
| 3(b) | ccctccctccctctcggcatcctctgc (SEQ ID NO: 6) | 1278 to 1304 |
| 4 | cctccctctcggcatcctctgctttgctct (SEQ ID NO: 7) | 1283 to 1312 |
| 5(a) | cggacggccgagcgaacgag (SEQ ID NO: 8) | 1162 to 1181 |
| 5(b) | cggccgagcgaacgagcctg (SEQ ID NO: 9) | 1166 to 1185 |
| 6(a) | ccagggcctccctccctccctctcggc (SEQ ID NO: 10) | 1269 to 1295 |
| 6(b) | ggagaggagagcttccccccctcccctt (SEQ ID NO: 11) | 1344 to 1370 |
| 6(c) | agaggagagcttccccccctcccttcc (SEQ ID NO: 12) | 1346 to 1372 |
| 6(d) | ggagagcttccccccctcccttccctc (SEQ ID NO: 13) | 1349 to 1375 |
| 6(e) | ccctcccttccctcggtcccttccccc (SEQ ID NO: 14) | 1362 to 1388 |
| 7 | gtactgtgcaaggagccccc (SEQ ID NO: 15) | 1039 to 1058 |
| 8 | ggccatagattttcgtgacga (SEQ ID NO: 16) | 949 to 969 |

FIGURE 4C

*Br2* Promoter

| Motif | Site | Position |
|---|---|---|
| 1 | gccactctgctgaggtgggggg (SEQ ID NO: 17) | 886 to 906 |
| 2 | tgatagaacgcaacgtgccgcatgcatccattcccattcgttttccacagt (SEQ ID NO: 18) | 597 to 647 |
| 3 | cagtctctctcactagttggattctt (SEQ ID NO: 19) | 685 to 711 |
| 4 | cctccctctccacctcatatgctttgctct (SEQ ID NO: 20) | 856 to 885 |
| 5(a) | cggaggagcgagcgagcctg (SEQ ID NO: 21) | 749 to 768 |
| 5(b) | ggagcgagcgagcctggcgg (SEQ ID NO: 22) | 753 to 772 |
| 6(a) | taanccaatccactcctcctccctctc (SEQ ID NO: 23) | 839 to 865 |
| 6(b) | nccaatccactcctcctccctctccac (SEQ ID NO: 24) | 842 to 868 |
| 6(c) | gcagaggagctcccccctccctcctctc (SEQ ID NO: 25) | 907 to 933 |
| 6(d) | agaggagctcccccctccctcctctccc (SEQ ID NO: 26) | 909 to 935 |
| 6(e) | gaggagctcccccctccctcctctcccc (SEQ ID NO: 27) | 910 to 936 |
| 6(f) | ggagctcccccctccctcctctccc ctc (SEQ ID NO: 28) | 912 to 938 |
| 7 | gtactgtgcaagtagggtcc (SEQ ID NO: 29) | 658 to 677 |
| 8 | gccgttagattttagtgacga (SEQ ID NO: 30) | 570 to 590 |

BRACHYTIC2 (BR2) PROMOTER FROM MAIZE AND METHODS OF USE

CROSS-REFERENCE TO RELATED APPLICATIONS

This application claims the benefit of U.S. Provisional Application No. 60/499,580, filed Sep. 2, 2003, which is hereby incorporated herein in its entirety by reference.

FIELD OF THE INVENTION

The invention relates to the genetic engineering of plants, particularly to the regulation of transgene expression in plants.

BACKGROUND OF THE INVENTION

Expression of heterologous DNA sequences in a plant host is dependent upon the presence of an operably linked promoter that is functional within the plant host. The type of promoter sequence chosen is based on when and where within the organism expression of the heterologous DNA is desired. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant. Genetically altering plants through the use of genetic engineering techniques to produce plants with useful traits thus requires the availability of a variety of promoters.

Frequently it is desirable to express a DNA sequence in particular tissues or organs of a plant. For example, increased resistance of a plant to infection by soil- and air-borne pathogens might be accomplished by genetic manipulation of the plant's genome to comprise a tissue-preferred promoter operably linked to a heterologous pathogen-resistance gene such that pathogen-resistance proteins are produced in the desired plant tissue. Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Additionally, it may be desirable to express a DNA sequence in plant tissues that are in a particular growth or developmental phase such as, for example, cell division or elongation. Such a DNA sequence may be used to promote or inhibit plant growth processes, thereby affecting the growth rate or architecture of the plant.

SUMMARY OF THE INVENTION

The invention provides compositions and methods for regulating gene expression in plants. The compositions include expression cassettes comprising a promoter of the invention operably linked to a polynucleotide molecule of interest. The promoters of the invention include the promoters of the Brachytic2 (Br2) and Dwarf3 (Dw3) genes and functional fragments and variants thereof.

The compositions of the invention find use in methods for regulating gene expression in a plant, particularly gene expression that is preferentially in elongating cells and/or elongating tissues or tissues that are known to undergo elongation such as, for example, the internodes of the stem or stalk of a plant and the silks and tassels of a maize plant. The compositions also find use in methods of preferentially directing the expression of an operably linked polynucleotide molecule of interest to vascular bundles, and/or the tissues or cells in the vicinity of such bundles. The methods involve stably incorporating into the genome of a plant cell an expression cassette comprising a promoter of the invention operably linked to a polynucleotide or gene of interest. The invention does not depend on a particular polynucleotide molecule of interest or that such a gene encodes a polypeptide. Thus, the promoters of the invention can be used to regulate the expression of sequences that encode polypeptides, thereby regulating the expression of the polypeptide itself in a plant. Similarly, the promoters of the invention can be operably linked to a gene or nucleotide sequence of interest for antisense expression, thereby lowering the expression of a target gene in a plant. If such a target gene encodes a polypeptide, then the level of said polypeptide can be reduced in the plant. Thus, the methods of the invention find further use in regulating the expression of a polypeptide of interest in at least one cell, tissue, or organ of a plant in which decreased expression of the polypeptide is desired.

Additionally provided are transformed plants, plant tissues, plant cells, and seeds. Such transformed plants, tissues, cells, and seeds comprise stably incorporated in their genomes at least one nucleotide molecule of the invention.

BRIEF DESCRIPTION OF THE DRAWINGS

FIG. 1A illustrates the portion of the Br2 genomic sequence that was amplified by PCR to produce the isolated Br2 promoter. The regions corresponding to the forward and reverse PCR primers are underlined and in bold. The TATAA box and the translational start codon (ATG) are in bold. The GTTC box is underlined. The entire sequence depicted in FIG. 1A is also provided in the sequence listing as SEQ ID NO: 33.

FIG. 1B provides the sequence of the forward (GSP-F1) (SEQ ID NO: 34) and reverse (GSP-R1) (SEQ ID NO: 35) primers used to amplify the Br2 promoter region.

FIG. 2 provides the nucleotide sequence of the promoter region of the Dw3 gene. The entire sequence depicted in FIG. 2 is also provided in the sequence listing as SEQ ID NO: 36.

FIG. 3 depicts the results of an alignment of the promoter regions of the maize Br2 gene (958 bp above ATG codon) and the *sorghum* Dw3 gene (1401 bp above ATG codon) using BestFit DNA Sequence Alignment Analysis. The TATA box and ATG codons are highlighted as bold letters. The Br2 promoter sequence in the alignment (upper strand) corresponds to nucleotides 1–947 of SEQ ID NO: 33. The Dw3 promoter sequence in the alignment (lower strand) corresponds to nucleotides 324–1375 of SEQ ID NO: 36.

FIG. 4B provides the position and sequence of each of the conserved motifs of the Dw3 promoter that are illustrated in FIG. 4A. The position refers to the position within the nucleotide sequence of the Dw3 promoter of the invention.

FIG. 4C provides the position and sequence of each conserved motif in the Br2 promoter that are illustrated in FIG. 4A. The position refers to the position within the nucleotide sequence of the Br2 promoter of the invention.

DETAILED DESCRIPTION OF THE INVENTION

The present invention is drawn to compositions and methods for regulating gene expression in plants, particularly in organs of the plant body that are undergoing elongation, more particularly in elongating organs such as, for example, a stem or a stalk. In particular the invention provides methods and compositions that are useful for regulating the expression of a polynucleotide or gene of interest preferentially in plant cells and tissues that are elongating or are known to undergo elongation. The invention is based on the discovery that the promoter (FIG. 1A; SEQ ID NO:1) of the Br2 gene of maize can be used to direct the expression of an operably linked nucleotide sequence in a plant preferentially in the elongating cells and/or tissues of stems, tassels, and silks of a maize plant. As disclosed more fully hereinafter, the Br2 promoter can also be used to preferentially direct the expression of an operably linked polynucleotide molecule of interest in vascular bundles, and/or cells surrounding such bundles. The nucleotide sequence of the Br2 gene has been previously disclosed in WO 01/34819, which is herein incorporated in its entirety by reference. See also, copending U.S. patent application Ser. No. 10/101,388, filed Mar. 19, 2002, and U.S. patent application Ser. No. 09/711,562, filed Nov. 13, 2000, now abandoned; both of which are herein incorporated in their entirety by reference.

Figure 4A:
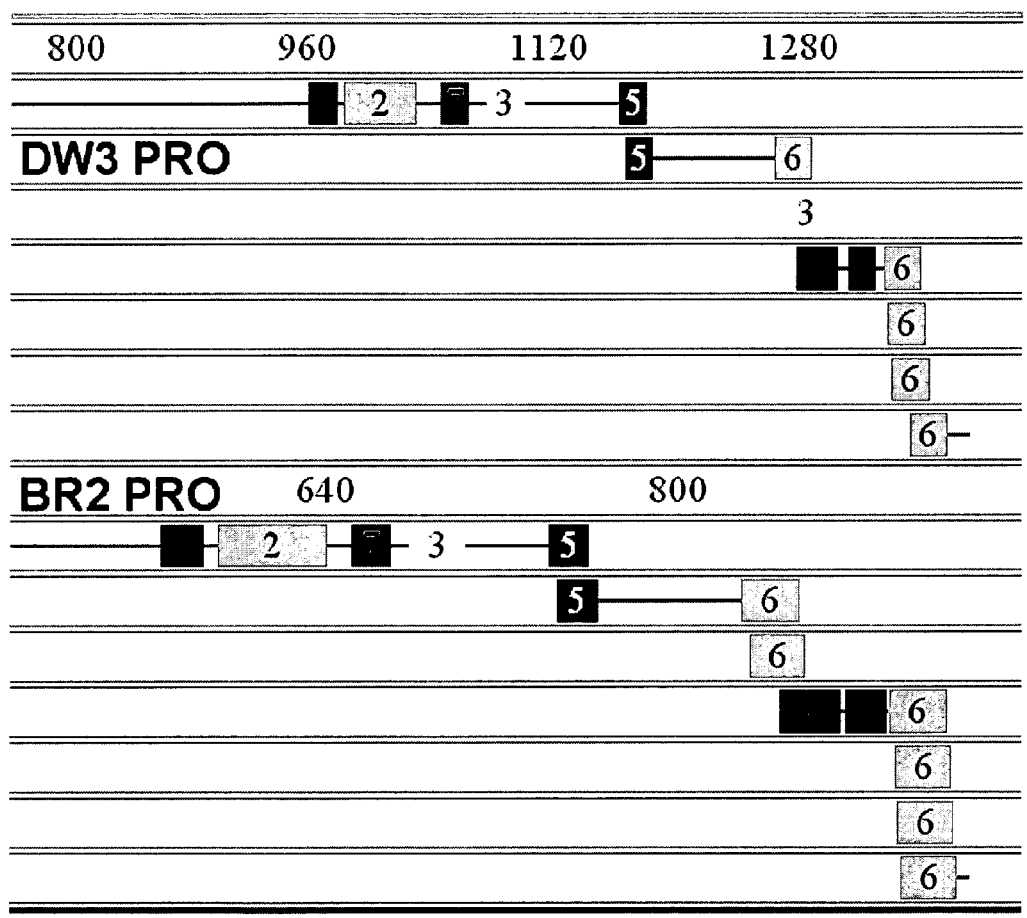
FIG. 4A illustrates the relative location of conserved sequence motifs in the sequences of the Dw3 promoter (DW3 PRO) and the Br2 promoter (BR2 PRO). The exact location and sequence of each of the motifs is indicated for the Dw3 and Br2 promoters in FIGS. 4B and 4C, respectively. The conserved motifs were identified using the SeqWeb MEME program of the GCG Wisconsin Package (Accelrys Inc., San Diego, Calif.)

In addition to the promoter of the Br2 gene of maize, the invention is further drawn to the promoter of the Dw3 gene of *sorghum* (FIG. 2; SEQ ID NO:2). Dw3 nucleotide sequences have been previously disclosed in WO 01/34818, which is herein incorporated in its entirety by reference. See also, copending U.S. patent application Ser. No. 09/711,619, filed Nov. 13, 2000; which is herein incorporated in its entirety by reference. The sorghum Dw3 gene is the *sorghum* ortholog of the maize Br2 gene. Genetic studies have previously revealed that the Dw3 and Br2 genes share a common function in *sorghum* and maize plants, respectively. Both sorghum plants that are homozygous for the recessive dw3 allele and maize plants that are homozygous for the recessive br2 allele display a reduced statute phenotype that is due to reduced internode elongation. The promoter regions of Dw3 and Br2 are also closely related. An alignment of the nucleotide sequences of the Dw3 and Br2 promoters reveals a 76.6% nucleotide sequence identity between the two monocot promoters (FIG. 3). In addition, there are eight conserved sequence motifs that are shared between these two promoters (FIGS. 4A–4C). Furthermore, the relative location of the conserved sequence motifs within each of these two promoters is also conserved (FIGS. 4A–4C). Given the high sequence identity between the Br2 and Dw3 promoters coupled with the presence of numerous conserved sequence motifs, the Dw3 promoter is also expected to direct preferentially the expression of an operably linked polynucleotide or gene of interest in elongating or elongated tissues in a manner similar to that for the Br2 promoter as disclosed herein below.

Compositions of the invention include nucleotide constructs or expression cassettes comprising the promoters of the Br2 and Dw3 genes. Such promoters find use in the regulation of operably linked heterologous nucleotide sequences, including sequences encoding proteins and antisense RNA. In particular, the present invention provides for isolated nucleic acid molecules comprising the nucleotide sequences shown in SEQ ID NOs: 1 and 2, the nucleotide sequences encoding the DNA sequences deposited in a bacterial host as Patent Deposit Nos. PTA-2645 and PTA-2646, and fragments and variants thereof.

Plasmids containing the nucleotide sequences of the invention were deposited with the Patent Depository of the American Type Culture Collection (ATCC), Manassas, Va., on Nov. 1, 2000 and assigned Patent Deposit Nos. PTA-2645 and PTA-2646. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid compositions. An "isolated" or "purified" nucleic acid molecule, or biologically active portion thereof, is substantially or essentially free from components that normally accompany or interact with the nucleic acid molecule as found in its naturally occurring environment. Thus, an isolated or purified nucleic acid molecule is substantially free of other cellular material, or culture medium when produced by recombinant techniques, or substantially free of chemical precursors or other chemicals when chemically synthesized. Optimally, an "isolated" nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

Fragments and variants of the disclosed nucleotide sequences are also encompassed by the present invention. By "fragment" is intended to mean a portion of the nucleotide sequence. Fragments of a nucleotide sequence may retain biological activity and hence promoter activity, particularly promoter activity that is preferentially in elongating cells and/or elongating tissues. Alternatively, fragments of a nucleotide sequence that are useful as hybridization probes generally do not retain biological activity. Thus, fragments of a nucleotide sequence may range from at least about 20 nucleotides, about 50 nucleotides, about 100 nucleotides, and up to the full-length nucleotide sequence of the invention.

A fragment of a Br2 or Dw3 promoter nucleotide sequence may encode a biologically active portion of a Br2 or Dw3 promoter, or it may be a fragment that can be used as a hybridization probe or PCR primer using methods disclosed below. A biologically active portion of a Br2 or Dw3 promoter can be prepared by isolating a portion of one of the Br2 or Dw3 promoter nucleotide sequences of the invention, and assessing the activity of the portion of the Br2 or Dw3 promoter. Nucleic acid molecules that are fragments of a Br2 promoter nucleotide sequence comprise at least 16, 20, 50, 75, 100, 150, 200, 250, 300, 350, 400, 450, 500, 550, 600, 650, 700, 800, 900 nucleotides, or up to the number of nucleotides present in a full-length Br2 promoter nucleotide sequence disclosed herein (for example, 961 nucleotides for SEQ ID NO: 1). Similarly, nucleic acid molecules that are fragments of a Dw3 promoter nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a full-length Dw3 promoter nucleotide sequence disclosed herein (for example, 1404 nucleotides for SEQ ID NO: 2).

By "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For nucleotide sequences, naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 40%, 50%, 60%, 65%, 70%, 75%, 80%, 85%, 90%, 91%, 92%, 93%, 94%, 95%, 96%, 97%, 98%, 99% or more sequence identity to that particular nucleotide sequence as determined by sequence alignment programs described elsewhere herein using default parameters.

Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein.

Thus, the genes and nucleotide sequences of the invention include both the naturally occurring sequences as well as mutant forms Variant nucleotide sequences also encompass sequences derived from a mutagenic and recombinogenic procedure such as DNA shuffling. With such a procedure, one or more different Br2 and/or Dw3 promoter nucleotide sequences can be manipulated to create a new Br2 or Dw3 promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire Br2 and/or Dw3 promoter sequences set forth herein or to fragments thereof are encompassed by the present invention. Such sequences include sequences that are orthologs of the disclosed sequences. By "orthologs" is intended to mean genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that have promoter activity and which hybridize under stringent conditions to the Br2 and/or Dw3 promoter sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the Br2 and/or Dw3 promoter sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire Br2 promoter sequence disclosed herein, or one or more portions thereof, may be used as a probe capable of specifically hybridizing to corresponding Br2 promoter sequences. Similarly, the entire Dw3 promoter sequence disclosed herein, or one or more portions thereof, may be used as a probe capable of specifically hybridizing to corresponding Dw3 promoter sequences. To achieve specific hybridization under a variety of conditions, such probes include sequences that are unique among Br2 and/or Dw3 promoter sequences and are optimally at least about 10 nucleotides in length, and most optimally at least about 20 nucleotides in length. Such probes may be used to amplify corresponding promoter sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. The duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.$+16.6(\log M)+0.41(\%$ GC$)-0.61(\%$ form$)-500/$L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Those of ordinary skill in the art recognize that the number and duration of post-hybridization washes are not considered critical factors in the specificity of hybridization. Typically, 1, 2, 3, 4, 5 or more sequential post-hybridization washes are conducted, with the duration of each of the washes being at least 1, 5, 10, 15, 20, 30, 45, 60, or more minutes.

In certain embodiments of the invention, functional fragments or functional variants of the exemplified Br2 or Dw3 promoters comprise at least one conserved promoter motif selected from the group consisting of a nucleotide sequence selected from the group consisting of the nucleotide sequences set forth in SEQ ID NOS: 3–32. The functional fragments and variants of the invention can comprise 1, 2, 3, 4, 5, 6, 7, 8, 9, 10, 11, 12, 13, 14, 15, 16, or more of the motifs. The motifs can occur in the nucleotide sequence of the fragment or variant in relatively the same position as the motif is known to occur in the Br2 or Dw3 promoter nucleotide sequences that are set forth in SEQ ID NOS: 1 and 2, respectively. The positions of the conserved motifs of the Br2 or Dw3 promoter nucleotide sequences are set forth in FIGS. 4A–4C and in SEQ ID NOS: 1 and 2 in the Sequence Listing. Alternatively, such motifs can occur in a different position in the nucleotide sequence of the fragment or variant than the motif is known to occur in the Br2 and Dw3 promoter nucleotide sequences that are set forth in SEQ ID NOS: 1 and 2, respectively.

In another embodiment of the invention, functional fragments and functional variants comprise a GARE motif (SEQ ID NO: 31) and a pyrimidine box (SEQ ID NO: 32) and can optionally comprise at least one additional motif, wherein the additional motif comprises a nucleotide sequence selected from the group consisting of the nucleotide sequences set forth in SEQ ID NOS: 3–30.

For the present invention, it is recognized that whether a motif is in a position in a second sequence that is relatively the same position as the motif occurs in a first sequence can be determined by aligning the first and second sequences by the alignment methods disclosed herein or other alignment methods known in the art. If the motif is in relatively the same position in the second sequence as it is in the first, the motifs of the second and first sequences will align to approximately the same place in the alignment of the two sequences.

The functional fragments and functional variants of the invention retain biological activity and hence promoter activity, particularly promoter activity that is preferentially in organs or tissues of the plant body that are undergoing elongation such as, for example, a stem or a stalk and/or promoter activity that is preferentially in vascular bundles, and/or the tissues or cells in the vicinity of such bundles.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local alignment algorithm of Smith et al. (1981) *Adv. Appl. Math.* 2:482; the global alignment algorithm of Needleman and Wunsch (1970) *J. Mol. Biol.* 48:443–453; the search-for-local alignment method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST, (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, optimally at least 80%, more optimally at least 90%, and most optimally at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 70%, 80%, 90%, or 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, optimally 80%, more optimally 85%, most optimally at least 90% or 95% sequence identity to the reference sequence over a specified comparison window. Typically, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The Br2 and Dw3 promoter sequences of the invention are provided in expression cassettes for the regulation of an operably linked gene in the plant of interest. The cassette will include 3' regulatory sequences operably linked to a Br2 or Dw3 promoter sequence of the invention. If desired, the cassette can include additional 5' regulatory sequences operably linked to the Br2 or Dw3 promoter nucleotides sequence of the invention. By "operably linked" is intended to mean a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be co-transformed into the organism. Alternatively, the additional gene(s) can be provided on multiple expression cassettes.

Such an expression cassette is provided with a plurality of restriction sites for insertion of the Br2 or Dw3 promoter nucleotide sequence to be under the transcriptional regulation of the regulatory regions. The expression cassette may additionally contain selectable marker genes.

The expression cassette will include in the 5'-3' direction of transcription, a transcriptional and translational initiation region (i.e., a Br2 or Dw3 promoter nucleotide sequence of the invention), a gene or nucleotide sequence of interest to be expressed, and a transcriptional and translational termination region (i.e., termination region) functional in plants. The nucleotide sequence of interest may be native or analogous, or foreign or heterologous, to the plant host and/or to the promoter nucleotide sequence of the invention. Additionally, the nucleotide sequence of interest may be the natural sequence or alternatively a synthetic sequence. By "native" or "analogous" to the plant host, it is intended to mean that the promoter is found in the native plant into which the promoter is introduced. For example, the Br2 promoter is "native" or "analogous" to maize (*Zea mays*). "By "foreign" or "heterologous" to the plant host, it is intended to mean that the promoter is not found in the native plant into which the promoter is introduced. Where the promoter is "foreign" or "heterologous" to the gene or nucleotide sequence of interest, it is intended to mean that the promoter is not the native or naturally occurring promoter for the operably linked gene or nucleotide sequence of interest. As used herein, a chimeric gene comprises a promoter of the invention operably linked, for either sense or antisense expression, to a nucleotide sequence that is heterologous to the promoter. Such a nucleotide sequence can be a coding sequence or fragment thereof, or a non-coding sequence such as, for example, the 5'- or 3'-untranslated region of a polynucleotide molecule of interest.

The invention encompasses constructs that comprise a promoter of the invention operably linked to a gene or nucleotide sequence of interest that is native to a plant host. When introduced into a plant for expression, such constructs would change expression levels of gene or nucleotide sequence of interest, or at least one gene product encoded thereby, in the plant or plant cell. Thus, the phenotype of the plant or plant cell is altered.

The termination region may be native to the promoter of the invention, may be native to the operably nucleotide sequence of interest, may be native to the plant host, or may be derived from another source (i.e., foreign or heterologous to the promoter, the nucleotide sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, a gene may be optimized for increased expression in the transformed plant. That is, the gene can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993)

Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology, Vol. 78* (Springer-Verlag, Berlin); Gill et al. (1988) *Nature* 334: 721–724. Such disclosures are herein incorporated by reference.

The above list of selectable marker genes is not meant to be limiting. Any selectable marker gene can be used in the present invention.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ an expression cassette or nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or RNA operably linked to 5' and 3' transcriptional regulatory regions.

In addition, it is recognized that methods of the present invention do not depend on the incorporation of the entire nucleotide construct into the genome, only that the phenotype of the plant or cell thereof is altered as a result of the introduction of the nucleotide construct into a cell.

In one embodiment, the nucleotide sequences of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romer et al. (1993) *Biochem. Biophys. Res. Commun.* 196:1414-1421; and Shah et al. (1986) Science 233:478–481.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769–780; Schnell et al. (1991) *J. Biol. Chem.* 266(5):3335–3342); 5-(enolpyruvyl)shikimate-3-phosphate synthase (EPSPS) (Archer et al. (1990) *J. Bioenerg. Biomemb.* 22(6):789–810); tryptophan synthase (Zhao et al. (1995) *J. Biol. Chem.* 270(11):6081–6087); plastocyanin (Lawrence et al. (1997) *J. Biol. Chem.* 272 (33):20357–20363); chorismate synthase (Schmidt et al. (1993) *J. Biol. Chem.* 268(36):27447–27457); and the light harvesting chlorophyll a/b binding protein (LHBP) (Lamppa et al. (1988) *J. Biol. Chem.* 263:14996–14999). See also Von Heijne et al. (1991) *Plant Mol. Biol. Rep.* 9:104–126; Clark et al. (1989) *J Biol. Chem.* 264:17544–17550; Della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481.

The expression cassettes of the invention can be used to transform the nucleus of plant cells. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923–926); and Lec1 transformation (WO 00/28058). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature*

Biotechnology 14:745–750 (maize via *Agrobacterium tumefaciens*); all of which are herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO 99/25821, WO 99/25854, WO 99/25840, WO 99/25855, and WO 99/25853, all of which are herein incorporated by reference. Briefly, the polynucleotide of the invention can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

The methods of the invention involve introducing a nucleotide construct into a plant. By "introducing" is intended to mean presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended to mean that the nucleotide construct introduced into a plant integrates into the genome of the plant and is capable of being inherited by progeny thereof. By "transient transformation" is intended to mean that a nucleotide construct introduced into a plant does not integrate into the genome of the plant.

The promoter nucleotide sequences and methods disclosed herein are useful in regulating the expression of any heterologous polynucleotide molecule of interest in a host plant in order to vary the phenotype of a plant. In particular, the promoters of the invention are useful for regulating the expressing of polynucleotides or genes that are involved in elongation growth, such as those that result in modified plant stature including, but not limited to, the maize d8 gene and its derivatives (WO 99/09174; Peng et al. (1999) *Nature* 400: 256–261; Accession No. AJ242530), the *Arabidopsis gai* gene (U.S. Pat. No. 6,307,126; Peng et al. (1997) *Genes Dev.* 11:3194–3205; Fu et al. (2001) *Plant Cell* 13: 1791–1802; Accession Nos. Y15193 and Y15194), the wheat rht gene (WO 99/09174; Peng et al. (1999) *Nature* 400: 256–261; Accession No. AJ242531), and the rice slr1 gene (Ikeda et al. (2001) *Plant Cell* 13:999–1010; Accession No. AB030956). In addition, the promoters of the invention are useful for regulating the expression of genes that function in vascular tissues, such as those that are involved in cell wall formation including, but not limited to, the maize CesA family of genes (Holland et al. (2000) *Plant Physiol.* 123: 1313–1323; Accession Nos. AF200525, AF200528, and AF200532). See also, WO 00/09706, herein incorporated by reference. The promoters of the invention find further use in directing the expression of polynucleotides or genes of interest in stem or stalk tissues including, but not limited to, those polynucleotides that encode gene products that are involved in stem or stalk strength, such as, for example, coding sequences for cell wall biosynthesis enzymes. Such cell wall synthesis enzymes include, but are not limited to, cellulose synthesis enzymes, hemi-cellulose synthesis enzymes, and any of the enzymes involved in lignin formation and deposition.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837–5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

A method for modulating the concentration and/or activity of a protein of interest in a plant is provided. In general, concentration and/or activity is increased or decreased by at least 1%, 5%, 10%, 20%, 30%, 40%, 50%, 60%, 70%, 80%, or 90% relative to a native control plant, plant part, or cell which did not have the sequence of the invention introduced. Modulation in the present invention may occur during and/or subsequent to growth of the plant to the desired stage of development. In specific embodiments, the protein of interest is modulated in monocots, particularly maize.

In specific embodiments, an expression cassette comprising a promoter of the invention operably linked to a polynucleotide molecule of interest is introduced into the plant cell. Subsequently, a plant cell having the introduced expression cassette is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity in the plant or part of protein of interest that is encoded for by the polynucleotide molecule of interest. Plant forming conditions are well known in the art and discussed briefly elsewhere herein.

In some embodiments, the activity of a protein of interest is reduced or eliminated by transforming a plant cell with an expression cassette that expresses a polynucleotide that inhibits the expression of the protein of interest. The polynucleotide may inhibit the expression of the protein of interest directly, by preventing translation of the messenger RNA encoding the protein of interest, or indirectly, by encoding a polypeptide that inhibits the transcription or translation of the gene that encodes the protein of interest. Methods for inhibiting or eliminating the expression of a gene in a plant are well known in the art, and any such method may be used in the present invention to inhibit the expression of the protein of interest in a plant, particularly a monocot plant.

In accordance with the present invention, the expression of a protein of interest is inhibited if the protein level of the protein of interest is less than 70% of the protein level of the same protein of interest in a plant that has not been genetically modified or mutagenized to inhibit the expression of that protein of interest. In particular embodiments of the invention, the protein level of the protein of interest in a modified plant according to the invention is less than 60%, less than 50%, less than 40%, less than 30%, less than 20%, less than 10%, or less than 5% of the protein level of the same protein in a plant that is not a mutant or that has not been genetically modified to inhibit the expression of that protein. The expression level of the protein of interest may be measured directly, for example, by assaying for the level of protein of interest expressed in the plant cell or plant, or indirectly, for example, by measuring enzyme activity of the protein of interest in the plant cell or plant using any known method.

In other embodiments of the invention, the activity of the protein of interest is reduced or eliminated by transforming a plant cell with an expression cassette comprising a polynucleotide encoding a polypeptide that inhibits the activity of the protein of interest. The activity of a protein of interest is inhibited according to the present invention if the activity of the protein of interest is less than 70% of the activity of the same protein in a plant that has not been genetically modified to inhibit the activity of that protein. In particular embodiments of the invention, the activity of the protein of interest in a modified plant according to the invention is less than 60%, less than 50%, less than 40%, less than 30%, less than 20%, less than 10%, or less than 5% of the activity of the same protein in a plant that that has not been genetically modified to inhibit the expression of that protein. The activity of a protein of interest is "eliminated" according to the invention when it is not detectable by the any known assay methods.

Thus, many methods may be used to reduce or eliminate the activity of a protein of interest. More than one method may be used to reduce the activity of a single protein of interest. In addition, combinations of methods may be employed to reduce or eliminate the activity of two or more different proteins of interest.

Non-limiting examples of methods of reducing or eliminating the expression of a protein of interest are given below.

Reduction of the activity of specific genes (also known as gene silencing or gene suppression) is desirable for several aspects of genetic engineering in plants. Many techniques for gene silencing are well known to one of skill in the art, including, but not limited to, antisense technology (see, e.g., Sheehy et al. (1988) *Proc. Natl. Acad. Sci. USA* 85:8805–8809; and U.S. Pat. Nos. 5,107,065; 5,453,566; and 5,759,829); cosuppression (e.g., Taylor (1997) *Plant Cell* 9:1245; Jorgensen (1990) *Trends Biotech.* 8(12):340–344; Flavell (1994) *Proc. Natl. Acad. Sci. USA* 91:3490–3496; Finnegan et al. (1994) *Bio/Technology* 12:883–888; and Neuhuber et al. (1994) *Mol. Gen. Genet.* 244:230–241); RNA interference (Napoli et al. (1990) *Plant Cell* 2:279–289; U.S. Pat. No. 5,034,323; Sharp (1999) *Genes Dev.* 13:139–141; Zamore et al. (2000) *Cell* 101:25–33; and Montgomery et al. (1998) *Proc. Natl. Acad. Sci. USA* 95:15502–15507), virus-induced gene silencing (Burton et al. (2000) *Plant Cell* 12:691–705; and Baulcombe (1999) *Curr. Op. Plant Bio.* 2:109–113); target-RNA-specific ribozymes (Haseloff et al. (1988) *Nature* 334: 585–591); hairpin structures (Smith et al. (2000) *Nature* 407:319–320; WO 99/53050; WO 02/00904; and WO 98/53083); ribozymes (Steinecke et al. (1992) *EMBO J.* 11:1525; and Perriman et al. (1993) *Antisense Res. Dev.* 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes et al. (1999) *Trends Plant Sci.* 4:90–96; Dharmapuri and Sonti (1999) *FEMS Microbiol. Lett.* 179:53–59; Meissner et al. (2000) *Plant J.* 22:265–274; Phogat et al. (2000) *J. Biosci.* 25:57–63; Walbot (2000) *Curr. Opin. Plant Biol.* 2:103–107; Gai et al. (2000) *Nucleic Acids Res.* 28:94–96; Fitzmaurice et al. (1999) *Genetics* 153:1919–1928; Bensen et al. (1995) *Plant Cell* 7:75–84; Mena et al. (1996) *Science* 274:1537–1540; and U.S. Pat. No. 5,962,764); each of which is herein incorporated by reference; and other methods or combinations of the above methods known to those of skill in the art.

It is recognized that the promoters of the invention can be used to drive the expression of antisense constructions in a plant or plant cell to disrupt the expression of a gene encoding a protein of interest. Antisense constructions, complementary to at least a portion of the messenger RNA (mRNA) for a protein of interest can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used.

The promoters of the present invention can also be used to drive expression of a polynucleotide molecule in the sense orientation to suppress the expression of an endogenous gene encoding a protein of interest in a plant. Such a polynucleotide molecule comprises all or part of the coding region for the protein of interest. Methods for suppressing gene expression in plants using polynucleotides in the sense orientation are known in the art. The methods generally involve transforming plants with a DNA construct comprising a promoter that drives expression in a plant operably linked to at least a portion of a polynucleotide that corresponds to the transcript of the endogenous gene. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference. Thus, many methods may be used to reduce or eliminate the activity of a protein of interest. More than one method may be used to reduce the activity of a single protein of interest. In addition, combinations of methods may be employed to reduce or eliminate the activity of the protein of interest.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus con torta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Optimally, plants of the present invention are crop plants (for example, corn, alfalfa, sunflower, *Brassica*, soybean, cotton, safflower, peanut, sorghum, wheat, millet, tobacco, etc.), more optimally corn, *sorghum*, and soybean plants, yet more optimally corn and sorghum plants.

The following examples are offered by way of illustration and not by way of limitation.

EXAMPLE 1

Br2 Promoter Isolation

To isolate a Br2 genomic clone containing the promoter region, a B73 partial Sau3AIII library in λ Dash II (Stratagene) was screened with a mixture of three gene-specific probes, representing the 5' end, the middle, and the 3' end of the Br2 gene. The positive clones were purified as single plaques and λ DNA was extracted. The λ DNA was further digested with different restriction enzymes. A 5.2 kb, EcoRI fragment containing the 5' end of the Br2 gene, including the promoter region, was subcloned and sequenced. Using gene-specific primers, about 1.0 kb sequence upstream of the initiation codon (AUG) was obtained (FIG. 1A). This sequence has a TATAA box and a GTTGG box (large protein) 137 bp and 245 bp upstream of initiation codon, respectively (FIG. 1A).

To amplify the Br2 promoter region, a PCR approach was used using B73 λ DNA as the template. Two oppositely orienting gene-specific primers (highlighted in bold and underlined in sequence; FIG. 1A) were designed covering around 800 bp upstream and 142 bp down stream of TATA box. The required restriction sites (EcoRI at the 5' end of the forward primer and a BamHI and a NcoI site in the 5' end of the reverse primer) were added in the primers. The nucleotide sequences and restriction sites therein for the forward primer (GSP-F1) and the reverse primer (GSP-R1) are shown in FIG. 1B.

PCR amplification was conducted consisting of 40 cycles of the following sequential steps in order: (i) denaturation at 94° C. for 1 min, (ii) annealing at 64° C. for 1 min, and (iii) synthesis at 72° C. for 2 min. An additional synthesis step of 10 min was added at the end of the 40$^{th}$ cycle. The PCR amplified fragments were gel separated on 1.4% agarose gel, purified, and cloned in a TA vector (Invitrogen). Four PCR amplified clones were sequenced and confirmed by alignment with sequence of Br2 genomic clone. The plasmid DNA was double digested with EcoRI and NcoI to isolate the Br2 promoter region for vector construction.

EXAMPLE 2

Dw3 Promoter Isolation

Southern blot and sequence analyses were used to select a DNA fragment which will contains the Dw3 promoter region. The size selected DNA fragment (13–14 kb EcoRI fragment) having the 5'-end of the Dw3 gene, including the promoter region, was cloned from Tall sorghum plant by making size fractionated library in lambda Dash II vector. The library was screened using exon 1 of the Dw3 gene as a DNA probe. The lambda DNA was isolated and directly sequenced by using gene-specific primers to provide the Dw3 promoter nucleotide sequence (FIG. 2).

The function of the Dw3 promoter will be analyzed in plants transformed with an expression cassette comprising the isolated Dw3 promoter operably linked to the GUS reporter gene essentially as described for the Br2 promoter in Example 4 below. Given the high sequence identity between the Br2 and Dw3 promoters (76.6%, FIG. 3) together with the presence of numerous conserved sequence motifs FIGS. 4A–4C), the Dw3 promoter is also expected to direct preferentially the expression of an operably linked polynucleotide or gene of interest in elongating or elongated tissues in a manner similar to that for the Br2 promoter as disclosed herein below.

EXAMPLE 3

The Br2 Promoter Contains Putative Gibberellin-Responsive Elements

Figure 5:
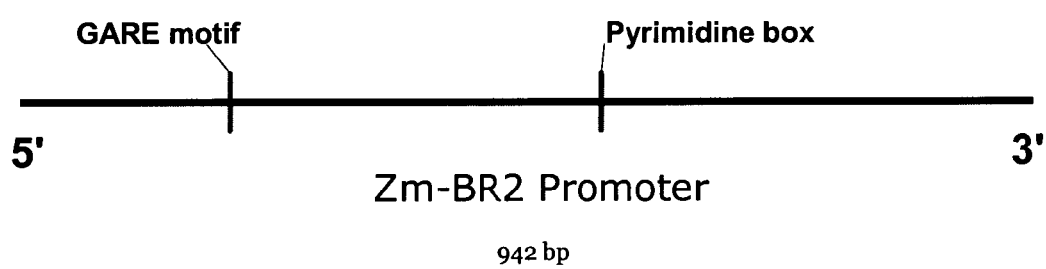
FIG. 5 is a schematic illustration of the promoter region of the maize Br2 gene indicating the relative position of two putative cis-elements, a GARE motif (AAACAGA, SEQ ID NO: 31) and a pyrimidine box (CCTTTT, SEQ ID NO: 32). Both the GARE motif and the pyrimidine box are also present in the Dw3 promoter (not shown)

The Br2 promoter sequence was analyzed with the Vector NTI motif display against a collection of published cis-elements of promoters. Two putative cis-elements, a GARE motif (AAACAGA, SEQ ID NO: 31) and a pyrimidine box (CCTTTT, SEQ ID NO: 32), were found in the Br2 promoter. These elements are believed to be involved in elongation growth in plants in response to the phytohormone, GA (GA is used herein to represent gibberellic acid and other gibberellins). The relative location of these gibberellin-responsive elements within the Br2 promoter region is shown in FIG. 5. The GARE motif was reported in cereal grain-expressed alpha-amylase genes (reviewed by Huttly and Phillips 1995, *Physiol. Plantarum* 95:310–317). The pyrimidine box was found in rice alpha-amylase gene. Both the GARE motif and the pyrimidine box have been implicated to be partially involved in sugar repression (Morita et al. 1998 FEBS Letter 423:81–85).

EXAMPLE 4

Vector Construction and Production to Transgenic Maize Plants

Figure 6:
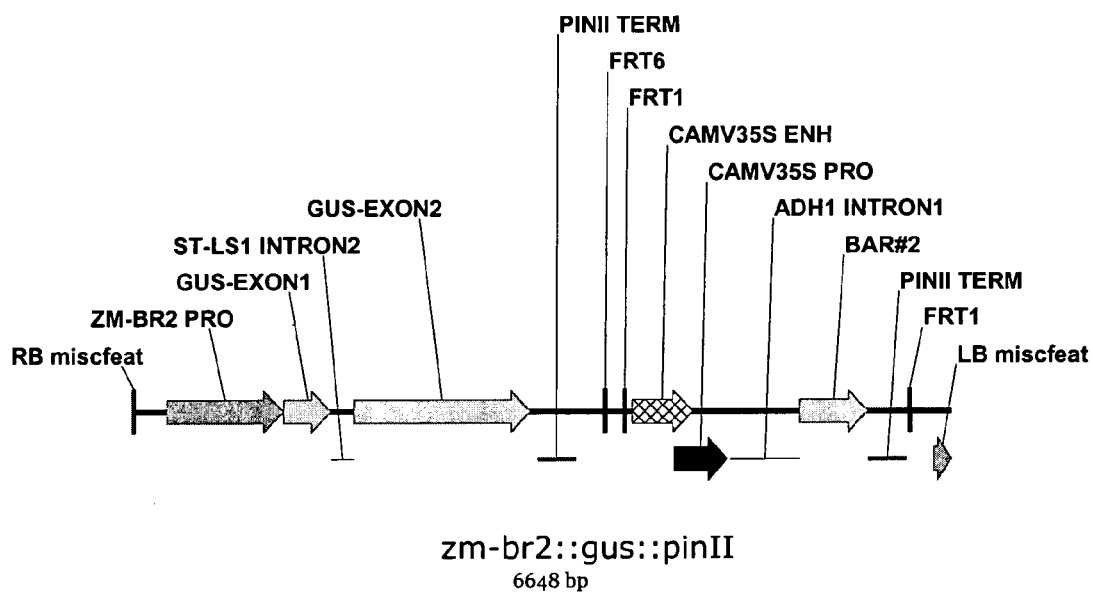
FIG. 6 is a schematic illustration of a vector for transformation of maize with the Br2 promoter operably linked to the GUS gene for expression in plants. The Br2-GUS expression cassette and the CaMV35S promoter-bar gene expression cassette lie between the T-DNA left (LB) and right (RB) borders.

An expression cassette comprising the isolated Br2 promoter was produced by operably linking a 944-bp fragment of the Br2 promoter (SEQ ID NO:1) to the GUS gene and pinII terminator. A schematic of this expression cassette is depicted in FIG. 6. This expression cassette was then linked to a selectable marker cassette containing a bar gene driven by CaMV 35S promoter and a pinII terminator (FIG. 6). Transgenic maize plants were produced by transforming Immature GS3 maize embryos this expression cassette using the *Agrobacterium*-based transformation method that is set forth in Example 7.

EXAMPLE 5

Specificity of the Br2 Promoter

Transgenic maize plants that were transformed with the construct depicted in FIG. 6 in which the Br2 promoter is operably linked to GUS coding sequences were produced essentially as described in Examples 4 and 7. These transgenic maize plants were analyzed for the expression of GUS by histochemical staining for GUS activity in the tissues from these plants. The histochemical staining revealed a vascular tissue-preferred expression pattern in transgenic maize plants. Out of the 25 $T_0$ events that were produced, 24 were sampled at various stages and GUS expression was examined by histochemical staining. Tissue samples were also set aside for molecular analysis.

Figure 7:
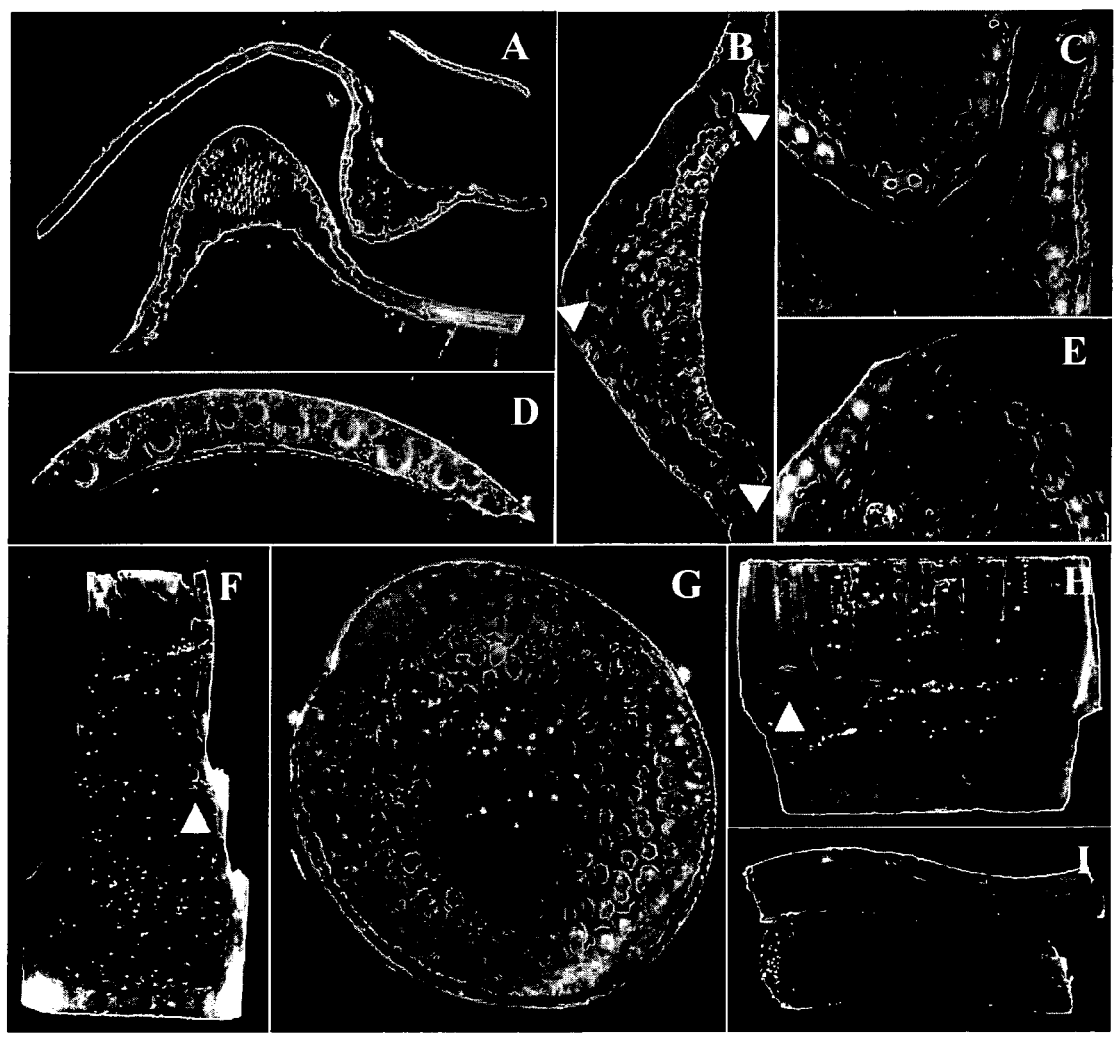
FIG. 7 is a photographic illustration of GUS reporter gene expression as driven by the Br2 promoter in transgenic maize plants. Illustrated are typical patterns representing events with high level of expression, observed in 24 independent events at $T_0$ generation. Plants were sampled between 3 and 7 weeks after transplanting. A) a leaf blade and midrib; B) leaf midrib showing stronger GUS expression (arrows) in each of the three vascular bundles at the bottom of the midrib and the connecting points of midrib to blades; C) spotty GUS expression in vascular bundles in leaf; D) pulvinus; E) GUS expression in parenchyma cells surrounding vascular bundles (note the absence of GUS staining in the vascular bundles); F) shoot apex, arrow indicates GUS expression in node; G) node; H) node, longitudinal section, arrow indicates GUS staining in vascular strand; and I) root segments showing GUS expression surrounding the central stele.

Of the 24 $T_0$ events analyzed for GUS expression, 17 events displayed strong expression, 5 events displayed medium expression and for 2 events, GUS expression was not detected. All 22 $T_0$ events that were positive for GUS expression had detectable GUS staining in leaf blade tissue (FIG. 7A). In most of these events, GUS staining was observed in vascular bundles with the stronger expression therein associated with larger vascular bundles (FIG. 7B). In some events, diffused GUS expression was also observed in cells surrounding the vascular bundles. In a few cases, GUS expression was not detected in all vascular bundles (FIG. 7C), or not detected in any vascular bundles, but rather in the cells surrounding the vascular bundles (FIG. 7F). Expression was more variable in leaf sheath, but when there was expression it was always stronger in pulvinus than the rest of the sheath (FIG. 7D). Root expression was also variable, but all events displayed some GUS expression in the root (FIG. 7I). No root tip expression was detected, but one event had root cap GUS expression. GUS expression was not detected in other parts of the root tip. GUS expression was not detected in shoot apex. In some events, however, GUS expression was detected in vascular bundles in young nodes that are three or more nodes below apical meristem (FIG. 7F).

A similar expression pattern was also found in more mature nodes (FIG. 7H). The internode portion of the stalk had more or less uniform distribution of GUS staining (FIG. 7F lower portion). GUS expression in nodal plates was also somewhat uniform (FIG. 7G).

EXAMPLE 6

Expression of the Br2 in Maize Plants

Figure 8:
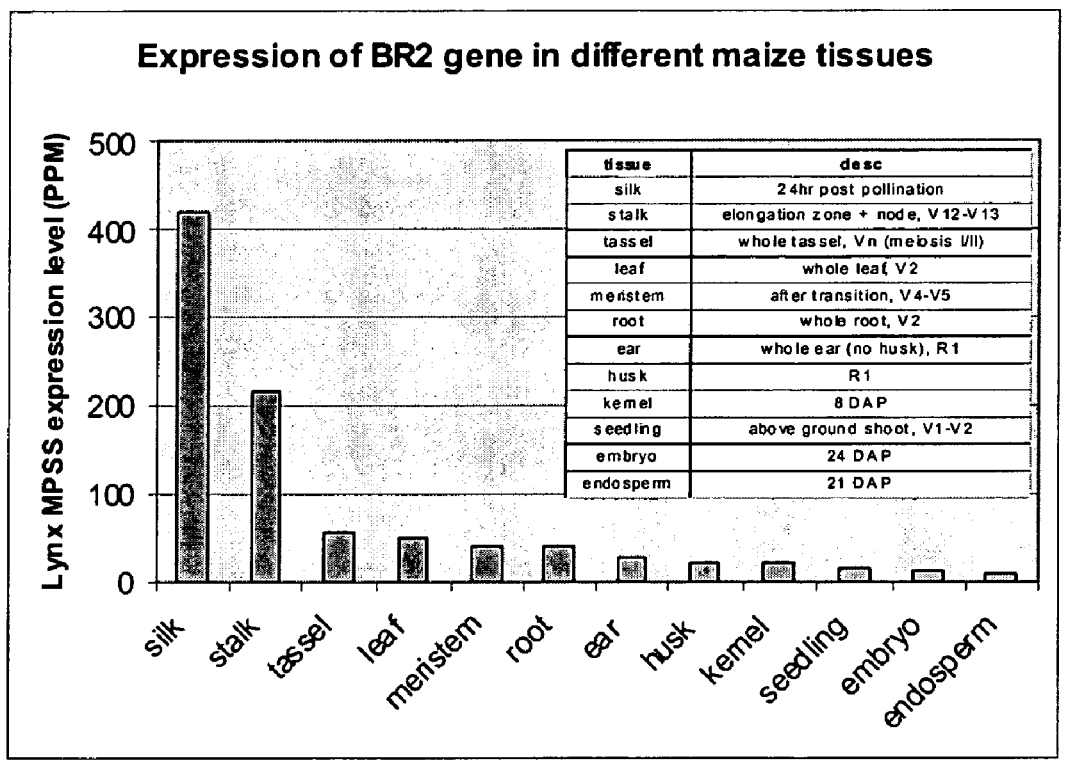
FIG. 8 is a graphical representation of the relative expression level of the Br2 gene among different tissues in maize. Adjusted PPM values from multiple libraries representing each tissue type were averaged. The inset box describes the sample and/or developmental stage of the maize plant sampled. "DAP" is days after pollination.

The expression of the endogenous Br2 gene was analyzed in maize to provide additionally information on the tissue-specificity for the Br2 promoter in plants. The Lynx MPSS (Massively Parallel Signature Sequencing) technology was used to examine Br2 gene expression at the mRNA level (Brenner et al., 2000 Nature Biotechnology 18:630–634). The results indicated that Br2 was expressed at relatively high levels in silk, stalk and tassel, as shown in the graph plotted with adjusted PPM values (FIG. 8).

Interestingly, these results indicate that the maize Br2 promoter does not function the same as the promoter of the related *Arabidopsis* gene, AtPGP1 (Accession No. X61370). Sidler et al. ((1998) *Plant Cell* 10:1623–1636) reported the results of the expression of an AtPGP1 promoter-GUS fusion gene in transgenic *Arabidopsis* plants via a standard histochemical staining method for the detection of GUS activity. Sidler et al. observed GUS staining in shoot and root apices and also in midribs of leaves, nodes of stems, and the elongation zone of roots. Sidler et al. confirmed the expression that was observed in the shoot apex by in situ hybridization.

Pairwise alignments of the promoter region of AtPGP1 (bases 1–938 of Accession No. X61370) with the Br2 promoter (SEQ ID NO: 1) and the Dw3 promoter (SEQ ID NO:2) using BestFit (maximum gap penalty of 12) yielded nucleotide sequence identities of 62.3% for AtPGP1-Br2 alignment and 72.0% for the AtPGP1-Dw3 alignment. Using the same method and parameters, an alignment of the Br2 promoter and the Dw3 promoter yielded a nucleotide sequence identity of 76.6%.

Pairwise alignments of the Br2 promoter (SEQ ID NO: 1) and the Dw3 promoter (SEQ ID NO:2) using BestFit (maximum gap penalty of 12) yielded a nucleotide sequence identitiy of 76.6%.

EXAMPLE 7

*Agrobacterium*-Mediated Transformation of Maize

For *Agrobacterium*-mediated transformation of maize with the expression cassette comprising the Br2 promoter operably linked to the GUS gene (see Example 3 and FIG. 6), the method of Zhao was employed (U.S. Pat. No. 5,981,840, and PCT patent publication WO 98/32326; the contents of which are hereby incorporated by reference). While the method below is described for the transformation of maize plants with the Br2 promoter GUS expression cassette, those of ordinary skill in the art recognize that this method can be used to produce transformed maize plants with any nucleotide construct or expression cassette of the invention that comprises a Br2 or Dw3 promoter operably linked to a polynucleotide molecule of interest for expression in a plant.

Briefly, immature embryos were isolated from maize and the embryos contacted with a suspension of *Agrobacterium*, where the bacteria are capable of transferring the Br2 promoter-GUS expression cassette (FIG. 6) to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step was included. In this resting step, the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus was recovered (step 4: the selection step). Optimally, the immature embryos were cultured on solid medium with a selective agent resulting in the selective growth of transformed cells. The resulting calli were then regenerated into plants by culturing the calli on solid, selective medium (step 5: the regeneration step).

EXAMPLE 8

Transformation and Regeneration of Transgenic Maize Plants

Immature maize embryos from greenhouse donor plants are bombarded with a plasmid containing the Br2 or Dw3 promoter operably linked to a polynucleotide molecule of interest and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% CLOROX bleach (5.25% sodium hypochlorite) plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5–cm target zone in preparation for bombardment.

Preparation of DNA

A plasmid vector comprising the Br2 or Dw3 promoter operably linked to a polynucleotide molecule of interest is made. See, for example, FIG. 6 and Example 4, supra. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for expression of the polynucleotide molecule of interest in, for example, elongating cells and/or elongating tissues.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l GELRITE (gellan gum) (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l GELRITE (gellan gum) (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l GELRITE (gellan gum) (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l BACTO agar (agar) (added after bringing to volume with polished D-I $H_2O$), sterilized and cooled to 60° C.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for regulating gene expression in a plant, said method comprising the steps of:
   (a) transforming at least one cell of a plant with an expression cassette comprising a promoter operably linked to a polynucleotide of interest, wherein the promoter is a nucleic acid molecule comprising the nucleotide sequence set forth in SEQ ID NO:1; and
   (b) regenerating said transformed cell into a transformed plant;
   wherein said promoter drives the expression of said polynucleotide of interest preferentially in elongating tissues of said plant, said elongating tissues selected from the group consisting of the elongating tissues of stems, tassels, and silks, or wherein said promoter drives the expression of said polynucleotide of interest in a part of said plant selected from the group consisting of a vascular bundle, cells surrounding a vascular bundle, a pulvinus, a leaf sheath, a root cap, a stalk internode, and a nodal plate.

2. An expression cassette comprising a promoter operably linked to a polynucleotide molecule of interest, wherein the promoter is a nucleic acid molecule comprising the nucleotide sequence set forth in SEQ ID NO:1 and wherein said promoter drives the expression of said polynucleotide of interest preferentially in elongating tissues of said plant, said elongating tissues selected from the group consisting of the elongating tissues of stems, tassels, and silks, or wherein said promoter drives the expression of said polynucleotide of interest in a part of said plant selected from the group consisting of a vascular bundle, cells surrounding a vascular bundle, a pulvinus, a leaf sheath, a root cap, a stalk internode, and a nodal plate.

3. A transformed plant comprising stably incorporated in its genome an expression cassette, said expression cassette comprising a promoter operably linked to a polynucleotide molecule of interest, wherein the promoter is a nucleic acid molecule comprising the nucleotide sequence set forth in SEQ ID NO:1 and wherein said promoter drives the expression of said polynucleotide of interest preferentially in elongating tissues of said plant, said elongating tissues selected from the group consisting of the elongating tissues of stems, tassels, and silks, or wherein said promoter drives the expression of said polynucleotide of interest in a part of said plant selected from the group consisting of a vascular bundle, cells surrounding a vascular bundle, a pulvinus, a leaf sheath, a root cap, a stalk internode, and a nodal plate.

4. A transformed plant cell comprising stably incorporated in its genome an expression cassette comprising a promoter operably linked to a polynucleotide molecule of interest, wherein the promoter is a nucleic acid molecule comprising the nucleotide sequence set forth in SEQ ID NO:1 and wherein said promoter drives the expression of said polynucleotide of interest preferentially in elongating tissues of said plant, said elongating tissues selected from the group consisting of the elongating tissues of stems, tassels, and silks, or wherein said promoter drives the expression of said polynucleotide of interest in a part of said plant selected from the group consisting of a vascular bundle, cells surrounding a vascular bundle, a pulvinus, a leaf sheath, a root cap, a stalk internode, and a nodal plate.

5. The method of claim 1, wherein said promoter drives the expression of said polynucleotide preferentially in vascular bundles of said plant.

6. The method of claim 1, wherein said polynucleotide encodes a polypeptide.

7. The method of claim 1, wherein said polynucleotide is operably linked to said promoter for the transcription of antisense RNA.

8. The method of claim 1, wherein said polynucleotide comprises the coding region of a gene selected from the group consisting of a maize d8 gene, an *Arabidopsis gai* gene, a wheat rht gene, a rice *slr*1 gene, a maize CesA gene, and a gene encoding a cell wall biosynthesis enzyme.

9. The method of claim 8, wherein the height of said transformed plant is decreased or increased when compared to an untransformed plant.

10. The method of claim 1, wherein said plant is a monocot or a dicot.

11. The method of claim 10, wherein said monocot is selected from the group consisting of maize, sorghum, wheat, rice, barley, rye, and millet.

12. The method of claim 10, wherein said dicot is selected from the group consisting of soybean, *Brassica* spp., sunflower, safflower, alfalfa, cotton, tomato, and *Arabidopsis*.

13. The transformed plant of claim 3, wherein said promoter drives the expression of said polynucleotide preferentially in vascular bundles of said plant.

14. The transformed plant of claim 3, wherein said polynucleotide encodes a polypeptide.

15. The transformed plant of claim 3, wherein said polynucleotide is operably linked to said promoter for the transcription of antisense RNA.

16. The transformed plant of claim 3, wherein said polynucleotide comprises the coding region of a gene selected from the group consisting of a maize d8 gene, an *Arabidopsis gai* gene, a wheat *rht* gene, a rice *slr*1 gene, a maize CesA gene, and a gene encoding a cell wall biosynthesis enzyme.

17. The transformed plant of claim 16, wherein the height of said transformed plant is decreased or increased when compared to an untransformed plant.

18. The transformed plant of claim 3, wherein said plant is a monocot or dicot.

19. The transformed plant of claim 18, wherein said monocot is selected from the group consisting of maize, sorghum, wheat, rice, barley, rye, and millet.

20. The transformed plant of claim 18, wherein said dicot is selected from the group consisting of soybean, *Brassica* spp., sunflower, safflower, alfalfa, cotton, tomato, and *Arabidopsis*.

21. A seed of the transformed plant of claim 3, wherein said seed comprises said expression cassette.

* * * * *

SEQUENCE LISTING

<160> NUMBER OF SEQ ID NOS: 32

<210> SEQ ID NO 1
<211> LENGTH: 944
<212> TYPE: DNA

<213> ORGANISM: Zea mays
<220> FEATURE:
<221> NAME/KEY: misc_feature
<222> LOCATION: (198)..(204)
<223> OTHER INFORMATION: GARE Motif
<220> FEATURE:
<221> NAME/KEY: misc_feature
<222> LOCATION: (545)..(550)
<223> OTHER INFORMATION: Pyrimidine Box
<220> FEATURE:
<221> NAME/KEY: TATA_signal
<222> LOCATION: (811)..(815)

<400> SEQUENCE: 1

```
gagtcggggg tagattctca aggctacata aatagttttt tttctagaat ggatgcattt      60
gttttaagag aaaaatgatg cacttggaat gcatcaagca aagggatgta agaatgttgg     120
aaaaacacat gaacccgtat cgcgagatgc ttatttatcc attctttatc acagtggatg    180
catatgcaac aaaaccaaaa cagatggtta gcgagtgaca gtatatagag atctaaagtt    240
gtccgacact tcatcggtaa aaaaagcagc ataaccgagt gaatggaaga aaaacgaatt    300
tctcatatac acagcaggtt ttcttaaaaa acgttatatc ggtattatat taagaagaga    360
ccaaaatatg gtcctgtcga gaaaatttct aaacattagt tctcatcacc agtgagccgt    420
caccatctag tttgcaacgg tccagttaga gtgcactcag gactcgcagc gagagaattt    480
ttttaatcaa gcctaaaatt cactttcgga caaatcgaac tactcataaa tattaaccat    540
gagacctttt cgccgcagca ggttttctat cggccgttag attttagtga cgatgaaaat    600
gatagaacgc aacgtgccgc atgcatccat tcccattcgt tttccacagt acatgtagga    660
gtactgtgca gtagggtcc gtacattcag tctctctcac tagttggact cttctactgc     720
tacaaagaca tgagctgccg ggaatgggaa ccggaggagc gagcgagcct gacggtctca    780
cacacacagt cacactccca agccaattat tataagaggc gagatgagca actccagctc    840
ttaaccaatc cactcctcct ccctctccac ctcctctgct ttgctctgcc actctgctga    900 ggtgggggc agaggagctc cccctcccte ctctcccctc ctcg                      944
```

<210> SEQ ID NO 2
<211> LENGTH: 1401
<212> TYPE: DNA
<213> ORGANISM: Sorghum bicolor
<220> FEATURE:
<221> NAME/KEY: misc_feature
<222> LOCATION: (176)..(181)
<223> OTHER INFORMATION: putative GARE Motif
<220> FEATURE:
<221> NAME/KEY: misc_feature
<222> LOCATION: (569)..(574)
<223> OTHER INFORMATION: putative GARE Motif
<220> FEATURE:
<221> NAME/KEY: misc_feature
<222> LOCATION: (820)..(828)
<223> OTHER INFORMATION: putative Pyrimidine Box
<220> FEATURE:
<221> NAME/KEY: TATA_signal
<222> LOCATION: (1229)..(1233)

<400> SEQUENCE: 2

```
agagcggttg ttcccaaaaa aggtgcaaat tctccaattc cccttcactc gaattttggc     60
cgtaagcgtg agtcataaat ctgacgaaat aaaaataatt gtacagtttg atcagaattg    120
acgggataat ctttgagtct agtagcccat gattggataa tatttgtcaa atacaaacga    180
aaaagctaag gccttgttta gatgcaccta aaacccaaa actgttacaa gattccccat     240
cacatcgaat cttgtggcac atgcatggaa tattaaatct agataaaaaa gataagtaat    300
```

-continued

```
tatacaggtt acctgtaaat cacggtacaa atctaaaaag acgaaaatgg tacggtgtca    360
aaatctaaaa agttttttgca tctaaacaag ggccttgttt agttcgcaaa attttttaag    420
atttcccgtc acatcgaatc tttggtcgta tgcatggagc attaaatata gataaaata     480 aaaactaatt gcacagttta cctgtaattt gtgagatgaa tcttttgagc ctagttactc    540
catgattgga caatgtttgt caaataaaaa caaaagtggt acagtagtca aaaaccaaag    600 ttttttgccaa ctaaacgagg cctaggccta attgcacatt ttgactgtaa atcgcgagac   660
gaatctttga aaacttttta tacgtcttgt ttagttcacc cttaaaaacc aaaattttt    720 caagattctc cgtcatcgga ttcttttgcc acaaacatgg cccttaaaat agatgaaaac   780
caaccttaat tgtacagttt gttgtaattc ggagaggaat cttttaatct agttactgta   840
tgattgaata atgtttgtta aataaaaatg aaagtgcctt acaccggtcc tcagcgaagg   900
aagaaacacg aatttttttgt agagcacaag cacaaaaggt ttcccatcgg ccatagattt   960
tcgtgacgac attgatagaa cgcaacgcgt agaatacatc cattctcgtt cgttttccac  1020
agtatgggga tgagtactgt actgtgcaag gagcccccccc gtacattcac agtctctctc  1080
actcgttgga ctcttcctct actcctacaa agacacacga ggctgcctgg gattggagcc  1140
ttgcactggg ccgacgccga ccggacggcc gagcgaacga gcctgaacca gagccctct  1200 catcagaggt ctcaagccgc aagccaatta taagaggcga gacaaagcaa ctcccaattc  1260
aatccacccc agggcctccc tccctccctc tcggcatcct ctgctttgct ctgcgccagc  1320
cactcttccg aggtggggggc agaggagagg agagcttccc cccctccctt ccctcggtcc  1380 cttccccccgg ccccccgatc g                                            1401
```

<210> SEQ ID NO 3
<211> LENGTH: 21
<212> TYPE: DNA
<213> ORGANISM: Sorghum bicolor

<400> SEQUENCE: 3

```
gccactcttc cgaggtgggg g                                               21
```

<210> SEQ ID NO 4
<211> LENGTH: 51
<212> TYPE: DNA
<213> ORGANISM: Sorghum biocolor

<400> SEQUENCE: 4

```
tgatagaacg caacgcgtag aatacatcca ttctcgttcg ttttccacag t              51
```

<210> SEQ ID NO 5
<211> LENGTH: 27
<212> TYPE: DNA
<213> ORGANISM: Sorghum biocolor

<400> SEQUENCE: 5

```
cagtctctct cactcgttgg actcttc                                         27
```

<210> SEQ ID NO 6
<211> LENGTH: 27
<212> TYPE: DNA
<213> ORGANISM: Sorghum bicolor

<400> SEQUENCE: 6

```
ccctccctcc ctctcggcat cctctgc                                         27
```

```
<210> SEQ ID NO 7
<211> LENGTH: 30
<212> TYPE: DNA
<213> ORGANISM: Sorghum bicolor

<400> SEQUENCE: 7
cctccctctc ggcatcctct gctttgctct                                    30

<210> SEQ ID NO 8
<211> LENGTH: 20
<212> TYPE: DNA
<213> ORGANISM: Sorghum bicolor

<400> SEQUENCE: 8
cggacggccg agcgaacgag                                               20

<210> SEQ ID NO 9
<211> LENGTH: 20
<212> TYPE: DNA
<213> ORGANISM: Sorghum bicolor

<400> SEQUENCE: 9
cggccgagcg aacgagcctg                                               20

<210> SEQ ID NO 10
<211> LENGTH: 27
<212> TYPE: DNA
<213> ORGANISM: Sorghum bicolor

<400> SEQUENCE: 10
ccagggcctc cctccctccc tctcggc                                       27

<210> SEQ ID NO 11
<211> LENGTH: 27
<212> TYPE: DNA
<213> ORGANISM: Sorghum bicolor

<400> SEQUENCE: 11
ggagaggaga gcttcccccc ctcccctt                                      27

<210> SEQ ID NO 12
<211> LENGTH: 27
<212> TYPE: DNA
<213> ORGANISM: Sorghum bicolor

<400> SEQUENCE: 12
agaggagagc ttccccccct cccttcc                                       27

<210> SEQ ID NO 13
<211> LENGTH: 27
<212> TYPE: DNA
<213> ORGANISM: Sorghum bicolor

<400> SEQUENCE: 13
ggagagcttc cccccctccc ttccctc                                       27

<210> SEQ ID NO 14
<211> LENGTH: 27
<212> TYPE: DNA
<213> ORGANISM: Sorghum bicolor

<400> SEQUENCE: 14
ccctcccttc cctcggtccc ttccccc                                       27
```

<210> SEQ ID NO 15
<211> LENGTH: 20
<212> TYPE: DNA
<213> ORGANISM: Sorghum bicolor

<400> SEQUENCE: 15
gtactgtgca aggagccccc                                                20

<210> SEQ ID NO 16
<211> LENGTH: 21
<212> TYPE: DNA
<213> ORGANISM: Sorghum bicolor

<400> SEQUENCE: 16
ggccatagat tttcgtgacg a                                              21

<210> SEQ ID NO 17
<211> LENGTH: 21
<212> TYPE: DNA
<213> ORGANISM: Zea mays

<400> SEQUENCE: 17
gccactctgc tgaggtgggg g                                              21

<210> SEQ ID NO 18
<211> LENGTH: 51
<212> TYPE: DNA
<213> ORGANISM: Zea mays

<400> SEQUENCE: 18
tgatagaacg caacgtgccg catgcatcca ttcccattcg ttttccacag t             51

<210> SEQ ID NO 19
<211> LENGTH: 26
<212> TYPE: DNA
<213> ORGANISM: Zea mays

<400> SEQUENCE: 19
cagtctctct cactagttgg attctt                                         26

<210> SEQ ID NO 20
<211> LENGTH: 30
<212> TYPE: DNA
<213> ORGANISM: Zea mays

<400> SEQUENCE: 20
cctccctctc cacctcatat gctttgctct                                     30

<210> SEQ ID NO 21
<211> LENGTH: 20
<212> TYPE: DNA
<213> ORGANISM: Zea mays

<400> SEQUENCE: 21
cggaggagcg agcgagcctg                                                20

<210> SEQ ID NO 22
<211> LENGTH: 20
<212> TYPE: DNA
<213> ORGANISM: Zea mays

<400> SEQUENCE: 22

```
ggagcgagcg agcctggcgg                                              20

<210> SEQ ID NO 23
<211> LENGTH: 27
<212> TYPE: DNA
<213> ORGANISM: Zea mays
<220> FEATURE:
<221> NAME/KEY: misc_feature
<222> LOCATION: (4)..(4)
<223> OTHER INFORMATION: The "n" at position 4 can be a, g, c, or t

<400> SEQUENCE: 23
taanccaatc cactcctcct ccctctc                                      27

<210> SEQ ID NO 24
<211> LENGTH: 27
<212> TYPE: DNA
<213> ORGANISM: Zea mays
<220> FEATURE:
<221> NAME/KEY: misc_feature
<222> LOCATION: (1)..(1)
<223> OTHER INFORMATION: The "n" at position 1 can be a, g, c, or t

<400> SEQUENCE: 24
nccaatccac tcctcctccc tctccac                                      27

<210> SEQ ID NO 25
<211> LENGTH: 27
<212> TYPE: DNA
<213> ORGANISM: Zea mays

<400> SEQUENCE: 25
gcagaggagc tccccctccc tcctctc                                      27

<210> SEQ ID NO 26
<211> LENGTH: 27
<212> TYPE: DNA
<213> ORGANISM: Zea mays

<400> SEQUENCE: 26
agaggagctc ccctccctc ctctccc                                       27

<210> SEQ ID NO 27
<211> LENGTH: 27
<212> TYPE: DNA
<213> ORGANISM: Zea mays

<400> SEQUENCE: 27
gaggagctcc cctccctcc tctcccc                                       27

<210> SEQ ID NO 28
<211> LENGTH: 27
<212> TYPE: DNA
<213> ORGANISM: Zea mays

<400> SEQUENCE: 28
ggagctcccc ctccctcctc tccccctc                                     27

<210> SEQ ID NO 29
<211> LENGTH: 20
<212> TYPE: DNA
<213> ORGANISM: Zea mays

<400> SEQUENCE: 29
gtactgtgca agtagggtcc                                              20
```

```
<210> SEQ ID NO 30
<211> LENGTH: 21
<212> TYPE: DNA
<213> ORGANISM: Zea mays

<400> SEQUENCE: 30
gccgttagat tttagtgacg a                                              21

<210> SEQ ID NO 31
<211> LENGTH: 7
<212> TYPE: DNA
<213> ORGANISM: Conserved cis-element of promoter

<400> SEQUENCE: 31 aaacaga                                                               7

<210> SEQ ID NO 32
<211> LENGTH: 6
<212> TYPE: DNA
<213> ORGANISM: Conserved cis-element of promoter

<400> SEQUENCE: 32 cctttt                                                                6
```